US00PP32053P2

(12) United States Plant Patent
Kolster et al.

(10) Patent No.: US PP32,053 P2
(45) Date of Patent: Aug. 11, 2020

(54) ***HYDRANGEA* PLANT NAMED 'HORTMASPOLI'**

(50) Latin Name: *Hydrangea macrophylla*
Varietal Denomination: Hortmaspoli

(71) Applicants: KOLSTER HOLDING B.V., Boskoop (NL); HORTEVE BREEDING B.V., Aalsmeer (NL)

(72) Inventors: Peter R. Kolster, Boskoop (NL); Cornelis P. Eveleens, Aalsmeer (NL)

(73) Assignees: Kolster Breeding B.V., Boskoop (NL); Horteve Breeding B.V., Aalsmeer (NL)

( * ) Notice: Subject to any disclaimer, the term of this patent is extended or adjusted under 35 U.S.C. 154(b) by 0 days.

(21) Appl. No.: 16/602,299

(22) Filed: Sep. 6, 2019

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 6/48
See application file for complete search history.

(56) References Cited

PUBLICATIONS

PLUTO Plant Variety Database Mar. 2, 2020.*

* cited by examiner

*Primary Examiner* — Annette H Para
(74) *Attorney, Agent, or Firm* — C. A. Whealy

(57) ABSTRACT

A new and distinct cultivar of *Hydrangea* plant named 'Hortmaspoli', characterized by its upright to somewhat outwardly spreading plant habit; moderately vigorous growth habit and moderate growth rate; freely branching habit with strong and thick sturdy stems; freely flowering habit; large mophead-type inflorescences with yellow green-colored sterile flowers with purple-colored centers and coarsely serrate margins; and good postproduction longevity.

2 Drawing Sheets

Figure 1:
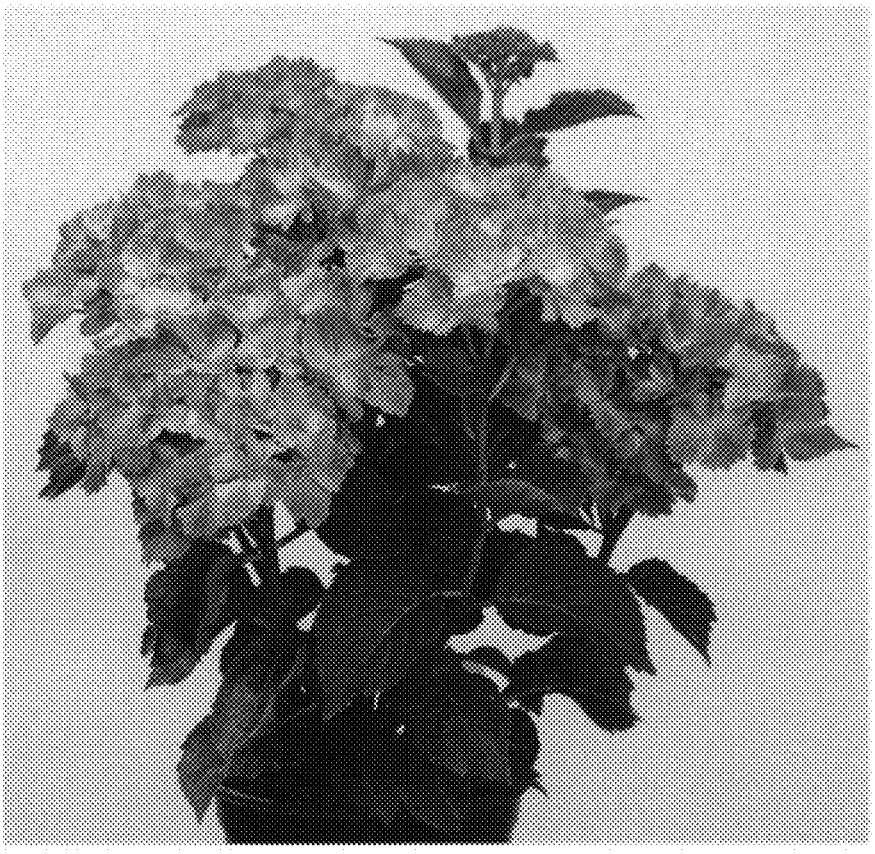

Botanical designation: *Hydrangea macrophylla.*
Cultivar denomination: 'HORTMASPOLI'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'Hortmaspoli'.

The new *Hydrangea* plant is a product of a planned breeding program conducted by the Inventors in Boskoop, The Netherlands. The objective of the breeding program was to create new potted and cut flower *Hydrangea* plants with large showy inflorescences with numerous attractive and unique sterile flowers and good postproduction longevity.

The new *Hydrangea* plant originated from a cross-pollination made by the Inventors in June, 2008 in Boskoop, The Netherlands, of a proprietary selection of *Hydrangea macrophylla* identified as code number 07-015-02, not patented, as the female, or seed, parent with a proprietary selection of *Hydrangea macrophylla* identified as code number 05-011-03, not patented, as the male, or pollen, parent. The new *Hydrangea* plant was discovered and selected by the Inventors as a single flowering plant from within the progeny of the stated cross-pollination in a controlled greenhouse environment in Boskoop, The Netherlands in July, 2010.

Asexual reproduction of the new *Hydrangea* plant by vegetative terminal cuttings in a controlled environment in Boskoop, The Netherlands since August, 2010 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hortmaspoli'. These characteristics in combination distinguish 'Hortmaspoli' as a new and distinct *Hydrangea* plant:

1. Upright to somewhat outwardly spreading plant habit.
2. Moderately vigorous growth habit and moderate growth rate.
3. Freely branching habit with strong and thick sturdy stems.
4. Freely flowering habit.
5. Large mophead-type inflorescences with yellow green-colored sterile flowers with purple-colored centers and coarsely serrate margins.
6. Good postproduction longevity.

Plants of the new *Hydrangea* can be compared to plants of the female parent selection. Plants of the new *Hydrangea* differ primarily from plants of the female parent selection in sterile flower color as sterile flower sepals of plants of the new *Hydrangea* are yellow green in color with purple-colored centers whereas sterile flower sepals of plants of the female parent selection are pink in color. In addition, sterile flower sepals of plants of the new *Hydrangea* have coarsely serrate margins whereas sterile flower sepals of plants of the female parent selection have entire margins.

Plants of the new *Hydrangea* can be compared to plants of the male parent selection. Plants of the new *Hydrangea* differ primarily from plants of the male parent selection in sterile flower color as sterile flower sepals of plants of the new *Hydrangea* are yellow green in color with purple-colored centers whereas sterile flower sepals ofplants ofthe male parent selection are green in color. In addition, sterile flower sepals of plants of the new *Hydrangea* have more coarsely serrate margins than sterile flower sepals of plants of the male parent selection.

Plants of the new *Hydrangea* can be compared to plants of *Hydrangea macrophylla* 'Hokomathyst', disclosed in U.S. Plant Pat. No. 22,261. Plants of the new *Hydrangea* differ primarily from plants of 'Hokomathyst' in sterile flower color as sterile flower sepals of plants of the new *Hydrangea* are yellow green in color with purple-colored centers whereas sterile flower sepals ofplants of 'Hokomathyst' are red purple in color with green-colored margins. In addition, sterile flower sepals of plants of the new *Hydrangea* are more coarsely serrate than sterile flower sepals of 'Hokomathyst'.

Plants of the new *Hydrangea* can be compared to plants of *Hydrangea macrophylla* 'Hokomac', disclosed in U.S. Plant Pat. No. 22,259. Plants of the new *Hydrangea* differ primarily from plants of 'Hokomac' in sterile flower color as sterile flower sepals of plants of the new *Hydrangea* are yellow green in color with purple-colored centers whereas sterile flower sepals of plants of 'Hokomac' are red purple and green in color. In addition, sterile flower sepals of plants of the new *Hydrangea* are more coarsely serrate than sterile flower sepals of 'Hokomac'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) is a side perspective view of a typical flowering plant of 'Hortmaspoli' grown in a container.

Figure 2:
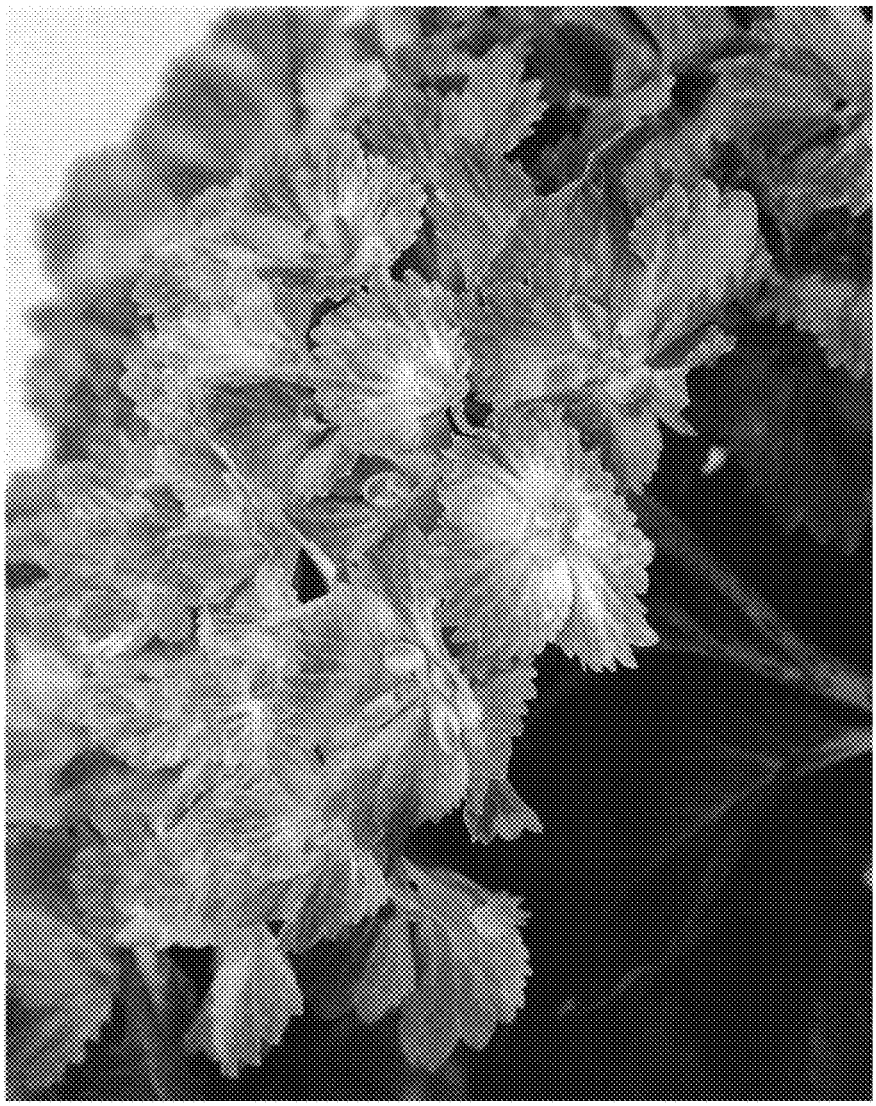

The photograph on the second sheet (FIG. 2 of 2) is a close-up view of a typical inflorescence of 'Hortmaspoli'.

DETAILED BOTANICAL DESCRIPTION

Plants used in the aforementioned photographs and in the following description were grown during the summer in 17-cm containers in a glass-covered greenhouse in Boskoop, The Netherlands and under cultural practices typical of commercial *Hydrangea* production. During the production of the plants, day temperatures ranged from 20° C. to 35° C. and night temperatures ranged from 10° C. to 22° C. Plants of the new *Hydrangea* were two years old when the photographs and description were taken. Plants of the new *Hydrangea* are not typically treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'Hortmaspoli'.

Parentage:

*Female, or seed, parent.*—Proprietary selection of *Hydrangea macrophylla* identified as code number 07-015-02, not patented.

*Male, or pollen, parent.*—Proprietary selection of *Hydrangea macrophylla* identified as code number 05-011-03, not patented.

Propagation:

*Type cutting.*—By vegetative terminal cuttings.

*Time to initiate roots, summer.*—About four weeks at temperatures about 15° C. to 25° C.

*Time to initiate roots, winter.*—About six weeks at temperatures about 15° C. to 21° C.

*Time to produce a rooted young plant, summer.*—About 100 days at temperatures about 15° C. to 25° C.

*Time to produce a rooted young plant, winter.*—About 140 days at temperatures about 15° C. to 21° C.

*Root description.*—Medium in thickness, fibrous; typically creamy white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright to somewhat outwardly spreading plant habit; overall plant shape, obovate; strong and sturdy lateral branches; moderately vigorous growth habit and moderate growth rate.

*Plant height.*—About 43.4 cm.

*Plant diameter or area of spread.*—About 45.8 cm.

Lateral branch description:

*Branching habit.*—Freely branching habit about seven lateral branches develop per plant; pinching will enhance branching.

*Length.*—About 24.9 cm.

*Diameter.*—About 6 mm.

*Internode length.*—About 5.5 cm.

*Texture.*—Smooth, glabrous; fully developed, woody.

*Aspect.*—Varying from upright to about 60° from vertical.

*Strength.*—Strong, sturdy.

*Color.*—When developing: Close to 144B. Developed: Close to 146D; at the internodes, occasionally tinged with close to N186C; when woody, close to 199B to 199D.

*Lenticels.*—Density: Dense. Length: About 1.5 mm. Diameter: About 1 mm. Color: Close to N186C.

Leaf description:

*Arrangement.*—Opposite, simple.

*Length.*—About 9.9 cm.

*Width.*—About 7.3 cm.

*Shape.*—Broadly ovate.

*Apex.*—Apiculate.

*Base.*—Obtuse to very short attenuate.

*Margin.*—Serrate.

*Texture, upper surface.*—Smooth to slightly rugose, glabrous.

*Texture, lower surface.*—Smooth to moderately rugose, glabrous.

*Venation pattern.*—Pinnate.

*Color.*—Developing leaves, upper surface: Close to between 137B and 143A. Developing leaves, lower surface: Close to 146B. Fully expanded leaves, upper surface: Close to 137A; venation, close to 147C. Fully expanded leaves, lower surface: Close to between 144A and 147B; venation, close to 145B.

*Petioles.*—Length: About 1.7 cm. Diameter: About 4 mm. Texture and luster, upper and lower surfaces: Smooth, glabrous; slightly glossy. Color, upper surface: Close to 145A. Color, lower surface: Close to 145A; proximally, close to 144B.

Flower description:

*Flower type and habit.*—Showy sterile flowers and small inconspicuous fertile flowers arranged on mophead-type terminal panicles; panicles flattened globular in shape; fertile flowers face mostly upright and sterile flowers face upright to outwardly depending on their position in the inflorescence.

*Fragrance.*—None detected.

*Natural flowering season.*—Plants flower from late spring to late summer in The Netherlands.

*Flower longevity.*—Fertile flowers last about three days on the plant, fertile flowers not persistent; sterile flowers last about six weeks on the plant, sterile flowers persistent.

*Quantity of flowers.*—Freely flowering habit; about seven fertile flowers per panicle and about 70 sterile flowers per panicle.

*Panicle height.*—About 12.4 cm.

*Panicle diameter.*—About 18.3 cm.

*Fertile flower buds.*—Length: About 5 mm. Diameter: About 3 mm. Shape: Ovate. Color: Close to 145A.

*Sterile flower buds.*—Length: About 1 cm. Diameter: About 1.7 cm. Shape: Broadly cup-shaped. Color: Close to N144D.

*Fertile flower diameter.*—About 1.8 cm.

*Fertile flower depth (height).*—About 1.2 cm.

*Sterile flower diameter.*—About 5.5 cm.

*Sterile flower depth (height).*—About 3 cm.

*Petals, fertile flowers.*—Quantity and arrangement: Five in a single whorl. Length: About 1.3 cm. Width: About 8mm. Shape: Ovate, slightly concave. Apex: Acute. Base: Cuneate. Margin: Entire. Texture and luster, upper and lower surfaces: Smooth, glabrous; matte. Color: When opening and fully opened, upper surface: Close to 143B; towards the margins, close to 157C; color does not change with development. When opening and fully opened, lower surface: Close to 144B; towards the margins, close to 157C; color does not change with development.

*Petals, sterile flowers.*—Quantity and arrangement: About four, occasionally five, in a single whorl. Length: About 7 mm. Width: About 5 mm. Shape: Ovate, moderately concave. Apex: Acute to bluntly acute. Base: Cuneate. Margin: Entire. Texture and luster, upper and lower surfaces: Smooth, glabrous; matte. Color: When opening, upper and lower surfaces: Close to 145B fading towards the base to close to 145D. Fully opened, upper surface: Close to 97A fading towards the apex to close to 97D; color becoming closer to 145A and towards the margins and base, close to 96D, with development. Fully opened, lower surface: Close to 97C fading towards the margins and apex to close to 97B; color becoming closer to 145A and towards the margins and base, close to 97A, with development.

*Sepals, fertile flowers.*—Quantity and arrangement: About five in a single whorl. Length: About 6 mm. Width: About 4 mm. Shape: Ovate. Apex: Acute. Base: Cuneate. Margin: Proximally, entire; distally, serrate. Texture and luster, upper and lower surfaces: Smooth, glabrous; matte. Color: When opening, upper and lower surfaces: Close to 145A. Fully opened, upper surface: Close to 143A; color does not change with development. Fully opened, lower surface: Close to 143B; color does not change with development.

*Sepals, sterile flowers.*—Quantity and arrangement: Five, occasionally four, in a single whorl. Length: About 3.3 cm. Width: About 3.6 cm. Shape: Reniform. Apex: Acute. Base: Broadly cuneate. Margin: Coarsely serrate, moderately undulate. Texture and luster, upper and lower surfaces: Smooth, glabrous; matte. Color: When opening, upper surface: Close to 144A fading towards the base to close to 144B; venation, close to NN155D. When opening, lower surface: Close to between 145B and 147D; venation, close to 145D. Fully opened, upper surface: Close to 144A fading towards the mid-section, close to 144C; towards the base, close to N75B; with development, color becoming closer to 143A fading towards the base to close to 144A. Fully opened, lower surface: Close to between 144B and 146D; at the base, close to 75A to 75B; with development, color becoming closer to between 144B and 146C.

*Pedicels, fertile flowers.*—Length: About 5 mm. Diameter: About 1 mm. Strength: Moderately strong. Aspect: About 20° from vertical. Texture and luster: Smooth, glabrous; matte. Color: Lighter than between 148D and 197D.

*Pedicels, sterile flowers.*—Length: About 3.3 cm. Diameter: About 3 mm. Strength: Moderately strong. Aspect: About 27.5° from peduncle axis. Texture and luster: Moderately pubescent; matte. Color: Close to 75B; proximally, close to 145A to 145B.

*Reproductive organs, fertile flowers.*—Stamens: Quantity per flower: About ten. Filament length: About 6 mm. Filament color: Close to NN155D. Anther length: About 1 mm. Anther shape: Broadly oblong. Anther color: Close to 195D. Pollen amount: Scarce. Pollen color: Close to 161A. Pistils: Pistil quantity per flower: About three, occasionally two or four. Pistil length: About 2 mm. Stigma shape: Club-shaped. Stigma color: Close to 150D. Style length: About 1 mm. Style color: Close to 145A to 145C. Ovary color: Close to 150D.

*Reproductive organs, sterile flowers.*—Stamens: Quantity per flower: About eight. Filament length: About 2 mm. Filament color: Close to N155B. Anther length: About 0.75 mm. Anther shape: Broadly oblong. Anther color: Close to 164B. Pollen amount: None observed. Pistils: Pistil quantity per flower: About three, occasionally two. Pistil length: About 1 mm. Stigma shape: Club-shaped. Stigma color: Close to 148D. Style length: About 0.5 mm. Style color: Close to 97B. Ovary color: Close to 145B.

*Seeds.*—To date, seed development has not been observed on plants of the new *Hydrangea.*

Pathogen & pest resistance: To date, under commercial production conditions, plants of the new *Hydrangea* have not been observed to be resistant to pathogens and pests common to *Hydrangea* plants.

Temperature tolerance: Plants of the new *Hydrangea* have been observed to tolerate temperatures ranging from −20° C. to 35° C. and are suitable for USDA Hardiness Zones 5 to 9.

It is claimed:

1. A new and distinct *Hydrangea* plant named 'Hortmaspoli' as illustrated and described.

* * * * *